United States Patent
Hallahan et al.

(10) Patent No.: US 9,180,249 B2
(45) Date of Patent: Nov. 10, 2015

(54) METHOD AND DEVICE

(71) Applicant: Bimeda Research & Development Limited, Dublin (IE)

(72) Inventors: Stephen Hallahan, Dublin (IE); Nicholas McHardy, County Wicklow (IE); Brendan Smith, Dublin (IE); Louis Van Vessem, Hellevoetsluis (NL)

(73) Assignee: BIMEDA RESEARCH & DEVELOPMENT LIMITED, Dublin (IE)

( * ) Notice: Subject to any disclaimer, the term of this patent is extended or adjusted under 35 U.S.C. 154(b) by 0 days.

(21) Appl. No.: 13/713,225

(22) Filed: Dec. 13, 2012

(65) Prior Publication Data

US 2013/0116657 A1    May 9, 2013

Related U.S. Application Data

(63) Continuation of application No. 12/896,805, filed on Oct. 1, 2010, now Pat. No. 8,353,877, which is a continuation of application No. 11/047,758, filed on Feb. 2, 2005, now Pat. No. 7,828,765.

(60) Provisional application No. 60/540,336, filed on Feb. 2, 2004.

(30) Foreign Application Priority Data

May 24, 2004    (IE) .................................. 2004/0364

(51) Int. Cl.
    *A61M 5/19*        (2006.01)
    *A61D 1/02*        (2006.01)
    *A61M 5/178*      (2006.01)

(52) U.S. Cl.
    CPC .. *A61M 5/19* (2013.01); *A61D 1/02* (2013.01); *A61M 2005/1787* (2013.01)

(58) Field of Classification Search
    CPC . A61K 2300/00; A61K 45/06; A61K 9/0041; A61K 9/0019; A61B 5/418; A61M 25/00; A61M 25/0097; A61M 31/00; A61M 2005/31598; A61M 5/31596; A61M 2005/1787; A61M 2005/3128; A61D 1/02
    USPC ........................ 604/514, 191, 187, 81, 86–91
    See application file for complete search history.

(56) References Cited

U.S. PATENT DOCUMENTS 978,488 A * 12/1910 Roesch .......................... 604/204
2,728,704 A * 12/1955 Edds et al. .................... 424/114

(Continued)

FOREIGN PATENT DOCUMENTS

EP       0 076 068 A2     4/1983
EP       0 081 896 A2     6/1983

(Continued)

OTHER PUBLICATIONS

International Search Report issued in PCT International Application No. PCT/IE2005/000007 mailed May 18, 2005, 5 pages.

(Continued)

*Primary Examiner* — Emily Schmidt
(74) *Attorney, Agent, or Firm* — Finnegan, Henderson, Farabow, Garrett & Dunner LLP

(57) ABSTRACT

The invention relates to a method and device for treating or preventing or suppressing a disease or condition in a non-human animal. The method comprises the steps of providing a single delivery device containing two components for sequential delivery from the delivery device. A first component is delivered from the single delivery device into a teat canal of a non-human animal and subsequently the second component is delivered from the single delivery device into the teat canal. The components are delivered without substantial mixing of the components.

65 Claims, 13 Drawing Sheets

(56) References Cited

U.S. PATENT DOCUMENTS

| | | | |
|---|---|---|---|
| 2,869,544 A | | 1/1959 | Ratciiff et al. |
| 3,680,558 A | * | 8/1972 | Kapelowitz ............... 604/89 |
| 3,685,514 A | | 8/1972 | Cheney |
| 3,911,916 A | * | 10/1975 | Stevens ................. 604/191 |
| 3,912,806 A | | 10/1975 | Dowrick et al. |
| 3,914,419 A | * | 10/1975 | Haeger et al. ............ 514/52 |
| 3,923,058 A | * | 12/1975 | Weingarten ............. 604/191 |
| 3,934,586 A | | 1/1976 | Easton et al. |
| 4,011,312 A | * | 3/1977 | Reuter et al. ............ 514/152 |
| 4,049,830 A | | 9/1977 | Pugliese |
| 4,073,920 A | * | 2/1978 | Dowrick ................ 514/193 |
| 4,172,138 A | * | 10/1979 | Rhodes ................. 514/199 |
| 4,313,440 A | * | 2/1982 | Ashley ................. 604/191 |
| 4,331,146 A | | 5/1982 | Brignola |
| 4,344,967 A | | 8/1982 | Easton et al. |
| 4,439,184 A | * | 3/1984 | Wheeler ................ 604/90 |
| 4,464,174 A | * | 8/1984 | Ennis .................. 604/90 |
| 4,702,737 A | * | 10/1987 | Pizzino ................ 604/191 |
| 4,820,272 A | * | 4/1989 | Palmer ................. 604/110 |
| 4,850,970 A | * | 7/1989 | Sutherland ............. 604/117 |
| 4,983,634 A | * | 1/1991 | Corby .................. 514/622 |
| 5,009,640 A | * | 4/1991 | Pyret et al. ............ 604/117 |
| 5,053,020 A | * | 10/1991 | Manchester ............. 604/239 |
| 5,059,172 A | * | 10/1991 | Sutherland et al. ....... 604/73 |
| 5,102,388 A | * | 4/1992 | Richmond .............. 604/88 |
| 5,195,966 A | * | 3/1993 | Corby .................. 604/75 |
| 5,290,258 A | | 3/1994 | Ennis, III et al. |
| 5,415,648 A | * | 5/1995 | Malay et al. ............ 604/181 |
| 5,476,449 A | * | 12/1995 | Richmond .............. 604/87 |
| 5,593,384 A | | 1/1997 | Halem |
| 5,599,312 A | | 2/1997 | Higashikawa |
| 5,624,405 A | | 4/1997 | Futagawa et al. |
| 5,704,918 A | | 1/1998 | Higashikawa |
| 5,706,937 A | | 1/1998 | Futagawa et al. |
| 5,720,732 A | | 2/1998 | Whisson |
| 5,899,889 A | | 5/1999 | Futagawa et al. |
| 6,077,252 A | | 6/2000 | Siegel |
| 6,107,344 A | | 8/2000 | Loosemore |
| 6,142,976 A | | 11/2000 | Kubo |
| 6,270,482 B1 | | 8/2001 | Rosoff et al. |
| 6,436,444 B1 | * | 8/2002 | Richter et al. ........... 424/665 |
| 6,558,358 B2 | | 5/2003 | Rosoff et al. |
| 6,723,074 B1 | * | 4/2004 | Halseth ................ 604/201 |
| 6,997,910 B2 | * | 2/2006 | Howlett et al. .......... 604/191 |
| 7,828,765 B2 | | 11/2010 | Hallahan et al. |
| 2003/0060414 A1 | * | 3/2003 | McHardy et al. ......... 514/12 |
| 2003/0167041 A1 | | 9/2003 | Rosoff et al. |
| 2003/0236503 A1 | * | 12/2003 | Koenig et al. ........... 604/201 |
| 2004/0004316 A1 | | 1/2004 | Robertson |
| 2004/0138611 A1 | | 7/2004 | Griffiths et al. |
| 2005/0118156 A1 | * | 6/2005 | Woolverton ............ 424/94.6 |
| 2005/0245880 A1 | | 11/2005 | Howlett et al. |
| 2006/0052747 A1 | * | 3/2006 | Nishimura et al. ........ 604/85 |
| 2007/0077235 A1 | * | 4/2007 | Loomis et al. .......... 424/93.6 |
| 2007/0093421 A1 | * | 4/2007 | McHardy et al. ......... 514/12 |
| 2008/0233091 A1 | * | 9/2008 | Ross et al. ............. 424/93.45 |
| 2010/0099625 A1 | * | 4/2010 | McHardy et al. ......... 514/12 |

FOREIGN PATENT DOCUMENTS

| | | |
|---|---|---|
| EP | 0 271 306 A2 | 6/1988 |
| EP | 0 540 493 A1 | 5/1993 |
| EP | 0 755 663 | 1/1997 |
| EP | 0 971 690 B1 | 1/2000 |
| FR | 2 076 853 | 10/1971 |
| FR | 2 251 339 | 6/1975 |
| GB | 1 441 757 | 7/1976 |
| GB | 1 456 349 | 11/1976 |
| GB | 2 273 443 A | 6/1994 |
| GB | 2 273 655 | 6/1994 |
| GB | 2 273 441 B | 1/1997 |
| JP | H08-294532 A | 11/1995 |
| JP | H08-294532 A | 11/1996 |
| JP | 2003-299734 | 10/2003 |
| RU | 2 028 798 C1 | 2/1995 |
| WO | WO 94/13261 A1 | 6/1994 |
| WO | WO 95/31180 A1 | 11/1995 |
| WO | WO 96/32482 S1 | 10/1996 |
| WO | WO 98/26759 A1 | 6/1998 |
| WO | WO 02/11793 A1 | 2/2002 |
| WO | WO 02/076534 A1 | 10/2002 |
| WO | WO 03/022245 A1 | 3/2003 |
| WO | WO 03/045478 A1 | 6/2003 |
| WO | WO 2004/039434 A2 | 5/2004 |

OTHER PUBLICATIONS

Twomey, D.P. et al., "Protection Against *Staphylococcus aureus* Mastitis in Dairy Cows Using a Bismuth-Based Teat Seal Containing the Bacteriocin, Lacticin," J Dairy Sci., 83:1981-1988 (2000).

Meaney, W.J., "Dry period teat seal", Vet. Rec. (1976).

Meaney, W.J., "Effect of a Dry period teat seal on bovine udder infection", Ir. J. agric. Res. 16: 293-299 (1977).

Farnsworth, R.J., "Use of a teat sealer for prevention of intramammary infections in lactating cows", Jayma. vol. 177, No. 5, pp. 441-444 (1980).

Robert, P., Dictionnaires Le Robert, (1993).

Block, S., "Disinfection, Sterilisation, and Preservation," Lea & Febiger, Third Edition, pp. 346-398 (1983).

León-Barùa, et al., "In vitro and in vivo effects of three bismuth compounds on fermentation by colonic bacteria". Rev. of Infectious Diseases, 12.1 S24-S29, Jan.-Feb. 1990.

Vogt, K., et eh, "The minimum inhibitory concentrations of various bismuth salts against campylobacter pylon", Zbl. Baht. 271:304-310 (1989).

Kirk, R., et al., "Encyclopedia of Chemical Technology", The Interscience Encyclopedia, Inc., 2:77-84 and 538-540 (1948).

Kollidon, "Polyvinylpyrrolidone for the pharmaceutical industry", BASF, pp. 18-21 (1996).

Osmonds Teat Seal, submitted to the European Patent Office with an Opposition filed Jun. 4, 2003, against European Patent No. EP 0 971 690, which issued from European Patent Application No. 97949079.4, 4 pages.

ProAgri, http://www.proagri.co.za/uitgawe_07/7-05_Claxarnasteh.htm, Sep. 1996, 9 pages.

Berry, E.A. et al., "The effect of an intramammary teat seal on new intramarnmary infections", J. Dairy Sci., 85:2512-2520 (2002).

Notice of Opposition to Grant of a Patent submitted. By Borneo Research Ltd. in the Intellectual Property Office of New Zealand against corresponding New Zealand Patent Application No. 548748, Jan. 28, 2011, 3 pages.

Statement of Case submitted by Borneo Research Ltd. in the Intellectual Property Office of New Zealand against corresponding New Zealand Patent Application No. 548748, Mar. 31, 2011, 14 pages.

First Amended Notice of Opposition to Grant of a Patent submitted by Borneo Research Ltd. in the Intellectual Property Office of New Zealand against corresponding New Zealand Patent Application No. 548748, Mar. 31, 2011, 3 pages.

Marked-up Version of First Amended Notice of Opposition to Grant of a Patent submitted by Bornac Research Ltd. in the Intellectual Property Office of New Zealand against corresponding New Zealand Patent Application No. 548748, Mar. 31, 2011, 3 pages.

Third Party Observations submitted anonymously at the European Patent Office against corresponding European Patent Application No. 20050703040 on Aug. 19, 2013, 7 pages.

Amended Statement of Grounds from Norbrook Laboratories Limited in the UK Intellectual Property Ofice in connection with the application for revocation of corresponding UK Patent No. GB 2 429 159, received by Bimeda Research & Development Limited on Apr. 17, 2014, 19 pages.

Correspondence from Norbrook Laboratories Limited to the UK Intellectual Property Office in connection with the application for revocation of corresponding UK Patent No. GB 2 429 159, May 2, 2014, 21 pages.

Correspondence from Bimeda Research & Development Limited to the UK Intellectual Property Office in connection with the application for revocation of corresponding UK Patent No. GB 2 429 159, May 16, 2014, 4 pages.

(56) References Cited

OTHER PUBLICATIONS

Correspondence from the UK Intellectual Property Office in connection with the application for revocation of No. GB 2 429 159, May 28, 2013, 3 pages.

Clean version of Amended Counter-Statement from Bimeda Research & Development Limited in connection with the application for revocation of corresponding UK Patent No. GB 2 429 159, Jun. 25, 2014, 13 pages.

Marked-up version of Amended Counter-Statement from Bimeda Research & Development Limited in connection with the application for revocation of corresponding UK Patent No. GB 2 429 159, Jun. 25, 2014, 13 pages.

Letter from H. M. Chung on behalf of HGF Limited in connection with the application for revocation by Norbrook Laboratories Limited of corresponding UK Patent No. GB 2 429 159, dated Sep. 18, 2014, 1 page.

Expert Report of Dr. Stephen Terence Dunne in connection with the application for revocation by Norbrook Laboratories Limited of corresponding UK Patent No, GB 2 429 159, dated Sep. 11, 2014 (including Exhibit SD1, Annex to the Expert Report, and Figures 1-9:3, 40 pages.

Witness Statement of Francis E. O'Sullivan in connection with the application for revocation by Norbrook Laboratories Limited of corresponding UK Patent No. GB 2 429 169, dated Sep. 17, 2014, 5 pages.

Office Action dated Sep. 3, 2014, from the Canadian Intellectual Property Office for Canadian Patent Application No. 2,524,121, 3 pages.

Third Party Observations submitted anonymously at the European Patent Office against corresponding European Patent Application No. 20050703040 on. Aug. 19. 2013, 7 pages.

Translation of JP H08-294532 A, Nov. 12, 1995.

Statement of Grounds from Norbrook Laboratories Limited in the UK Intellectual Property Office in connection with the application for revocation of corresponding UK Patent No. GB 2 429 159 dated Nov. 8, 2013, 18 pages.

Patents Form 2 issued by the UK Intellectual Property Office in connection with the application for revocation of corresponding UK Patent No. GB 2 429 159 dated Nov. 8, 2013, 1 page.

Correspondence from the UK intellectual Property Office in connection with the application for revocation of corresponding UK Patent No. GB 2 429 159 dated Nov. 22, 2013, 3 pages.

Counter-Statement from Bimeda Research & Development Limited in connection with the application for revocation of corresponding UK Patent No. GB 2 429 159 dated Jan. 14, 2014, 11 pages.

Decision dated May 27, 2015 from British Intellectual Property Office in an application for revocation of corresponding GB Patent No. GB2429159 (24 pages).

Grounds of Appeal, of May 27, 2015, Decision, filed by Norbrook Laboratories Limited in the application for revocation of corresponding GB Patent No. GB2429159 (11 pages).

Bimeda's Additional Grounds for Upholding the Order filed in the application for revocation of corresponding GB Patent Application No. GB2429159 (2 pages).

\* cited by examiner

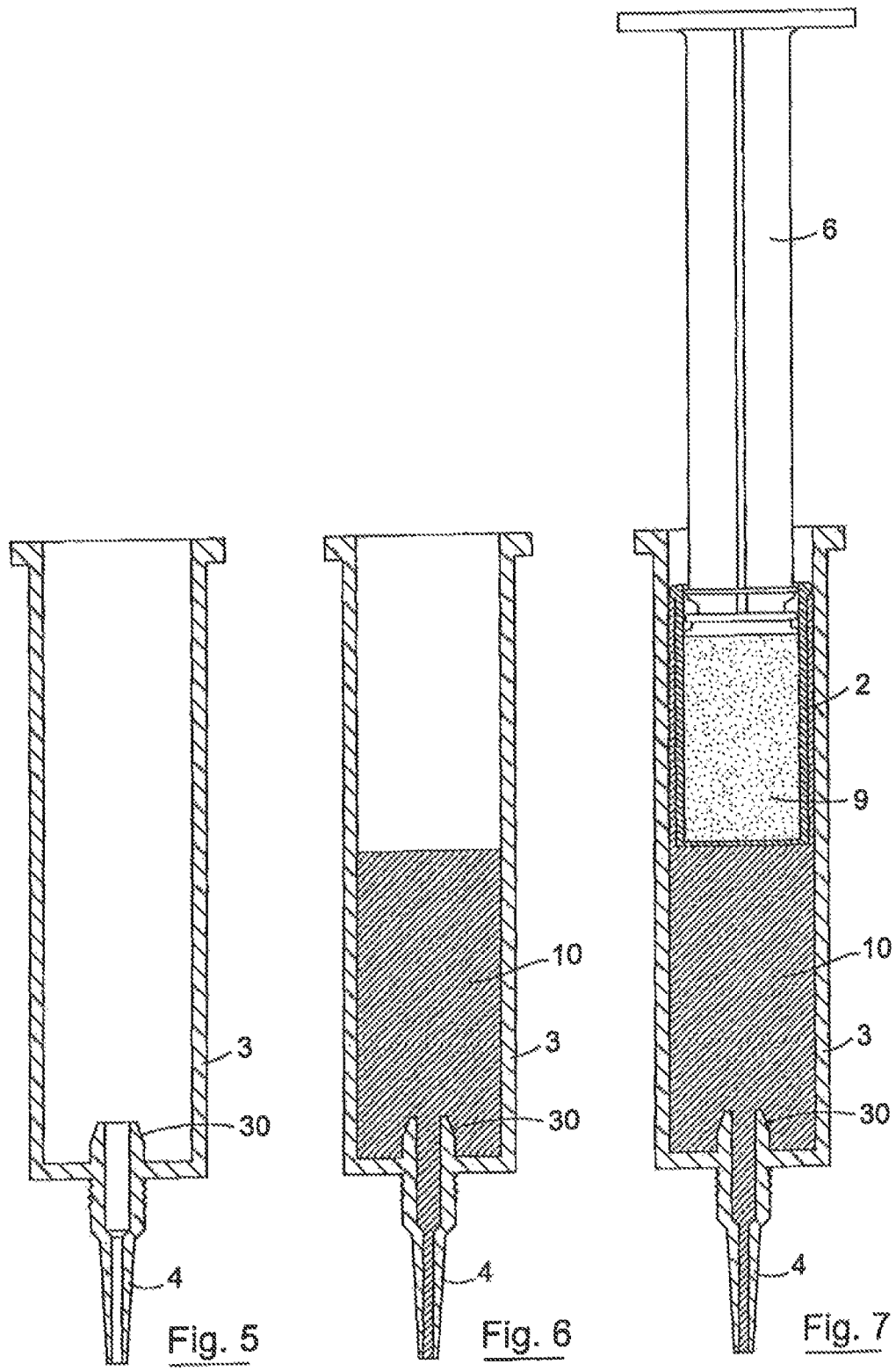

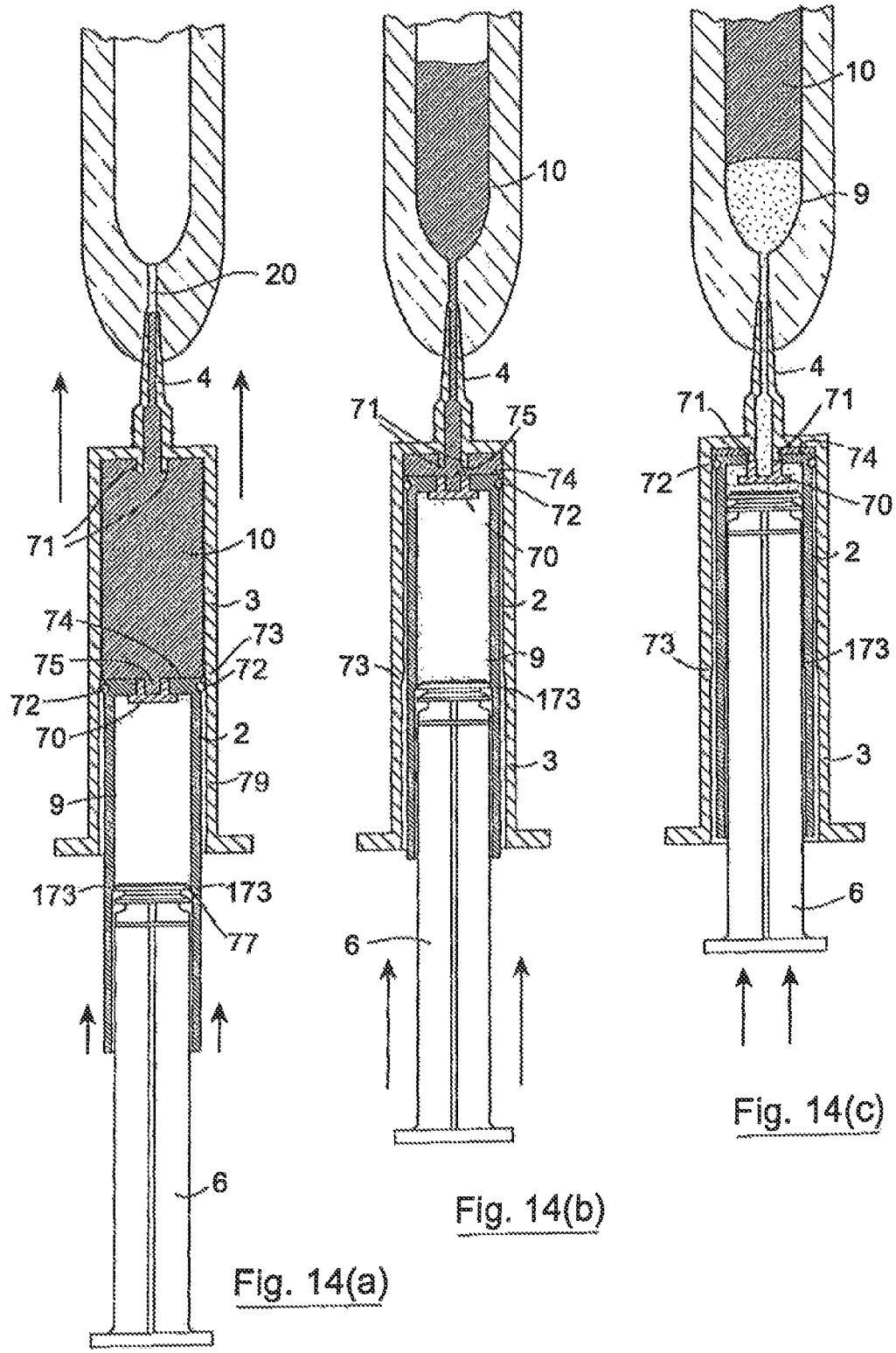

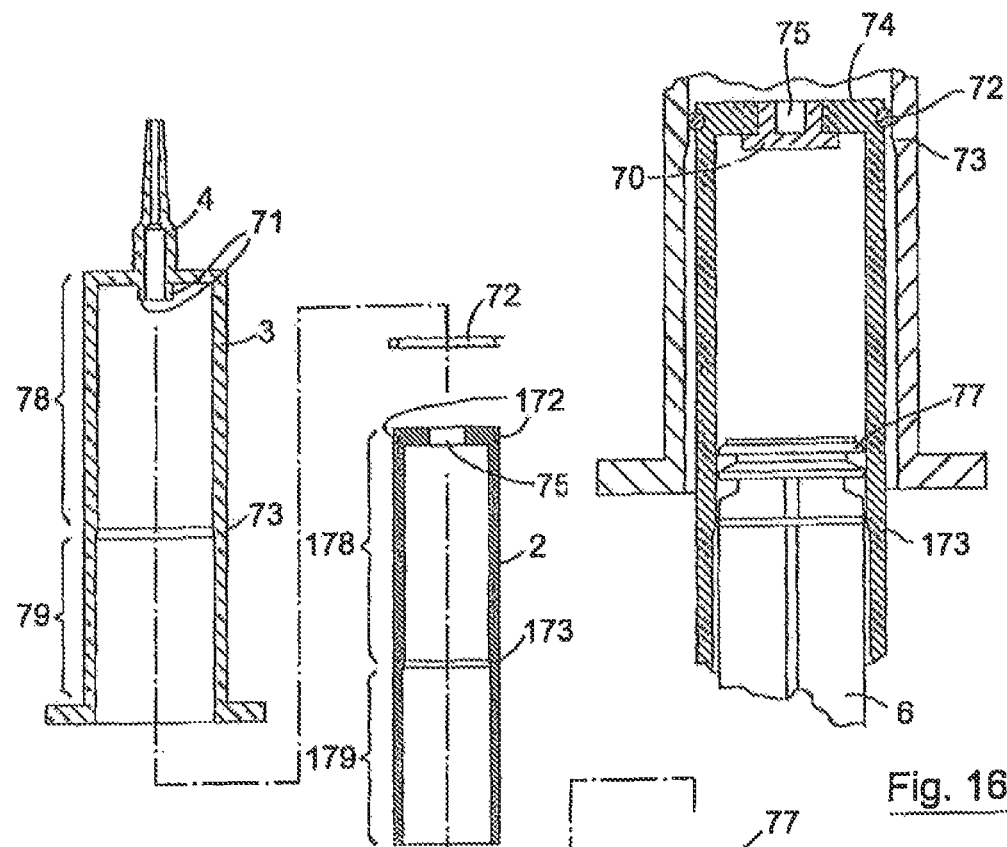
Fig. 16(a)
Fig. 15
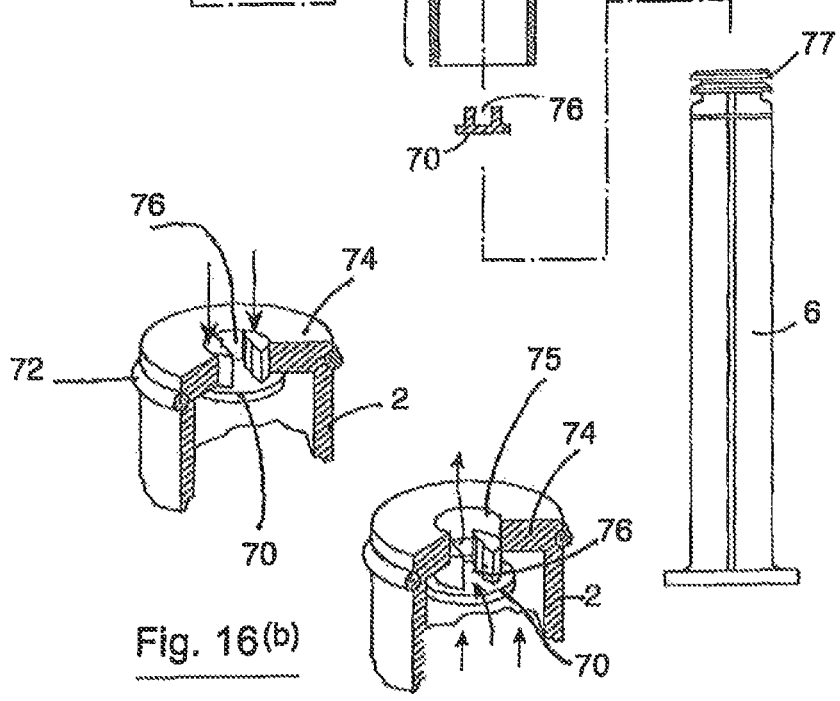
Fig. 16(b)
Fig. 16(c)

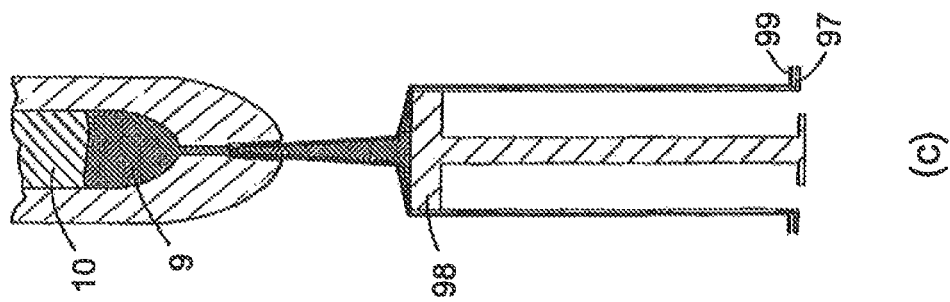
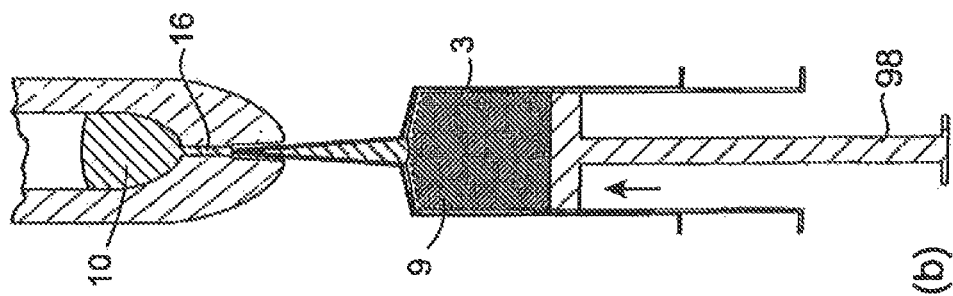
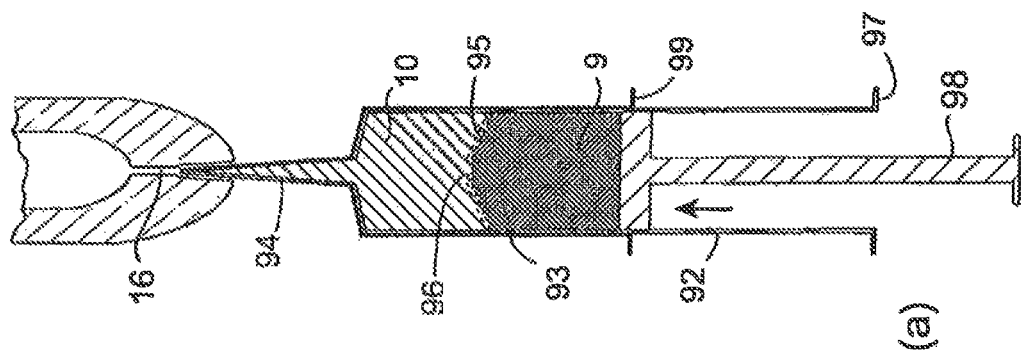
Fig. 20

METHOD AND DEVICE

This is a continuation of application Ser. No. 12/896,805, filed Oct. 1, 2010, which is a continuation of application Ser. No. 11/047,758, filed on Feb. 2, 2005, now U.S. Pat. No. 7,828,765, which claims the benefit of U.S. Provisional Application No. 60/540,336, filed Feb. 2, 2004, all of which are incorporated herein by reference in their entireties.

INTRODUCTION

The invention relates to a method and device for administering two components into the teat canal of a non-human animal.

Bovine mastitis is a severe, potentially fatal, inflammatory disease of the udder, caused by a broad range of infectious organisms, but most notably by various Gram positive bacteria of the genera *Staphylococcus* and *Streptococcus* and the Gram negative species, *Escherichia coli*. The infection usually enters the udder via the teat or streak canal. Mastitis is treated by a variety of antibiotic cerates, infused into the udder via the teat or streak canal. In severe cases, high doses of antibiotic are also given by injection. A high proportion of mastitic infections are contracted during the "dry" period, which precedes calving. The infection may later become clinically significant either during the dry period, or after calving when lactation has resumed.

It is known to treat mastitis using a twin injector pack, one injector containing an anti-bacterial formulation and a second injector containing a seal or barrier formulation. The antibacterial formulation is delivered first to the teat canal followed by delivery of the seal formulation forming a physical barrier in the teat canal against the entry of bacteria into the udder. These twin injector packs are sold under the name Teat Seal™. WO94/13261 and WO95/31180 describe the twin injectors in detail and are hereby incorporated by reference.

While the twin injector system provides an effective method to reduce the incidence of clinical mastitis administration of the injectors can be time consuming, doubles the risk of introducing extraneous environmental bacteria and doubles the risk of causing damage to the epithelium of the streak canal. The use of two injectors also increases the cost of treatment and creates additional non-degradable waste.

There is a need for an improved method and device for preventing intramammary disorders which will overcome at least some of these problems.

STATEMENTS OF INVENTION

According to the invention there is provided a method for treating or preventing or suppressing a disease or condition in a non-human animal comprising the steps of:
  providing a single delivery device containing two components for sequential delivery from the delivery device;
  delivering a first component from the single delivery device into a teat canal of a non-human animal; and
  subsequently delivering the second component from the single delivery device into the teat canal without substantial mixing of the components.

In one embodiment the delivery device comprises an injector device containing the two components, the components being separated by a barrier and the method comprises the steps of:
  delivering the first component from the injector device;
  at least partially releasing the barrier; and
  subsequently delivering the second component from the injector device.

In another embodiment the disease or condition is mastitis and the method of the invention is for treating or preventing a mastitis-causing micro-organism.

In a further embodiment the second component comprises a seal.

According to a further aspect the invention provides a method for treating, preventing or suppressing mastitis or a mastitis causing micro-organism comprising the steps of sequentially delivering from a single delivery device an antimicrobial formulation and a seal formulation into the teat canal of a non-human animal wherein the antimicrobial formulation and the seal formulation are delivered into the teat canal without substantial mixing of the formulations prior to delivery into the teat canal.

In one embodiment the seal formulation comprises a non-toxic heavy metal salt.

In another embodiment the seal formulation comprises greater than 40% by weight of the heavy metal salt.

In a further embodiment the seal formulation comprises between 50% and 75% by weight of the heavy metal salt.

In one embodiment the seal formulation comprises approximately 65% by weight of the heavy metal salt.

In another embodiment the heavy metal is bismuth.

In a further embodiment the salt is a sub-nitrate salt.

In one embodiment the seal formulation comprises a gel base.

In another embodiment the gel base is a gel based on aluminium stearate.

In a further embodiment the gel base includes liquid paraffin as a vehicle.

In one embodiment the first component comprises an antimicrobial.

In another embodiment the antimicrobial is selected from any one or more of betalactam antibiotics, polymyxins, glycopeptides, aminoglycosides, lincosamides, macrolides, pleuromutilins, "fenicols" such as chloramphenicol and florfenicol, tetracylcines, sulphonamides and potentiated sulphonamides such as mixtures of trimethoprim and one or more sulphonamide, quinolones and fluoroquinolones, ionophores, courmarins such as novobiocin, natural or synthetic peptides, aminoglycosides, antimicrobial peptides or antimicrobials, lantibiotics, or other products of bacteria and other micro-organisms.

In a further embodiment the betalactam is selected from any one or more of penicillin, modified penicillin such as cloxacillin, amoxycillin, cephalosporins or beta lactam antibiotics potentiated by beta lactamase inhibitors such as clavulanic acid.

In one embodiment the aminoglycoside is selected from any one or more of streptomycin, dihydrostreptomycin, neomycin, gentamycin, framycetin, aparamycin or kanamycin.

In another embodiment the antimicrobial is selected from any one or more of macrolide, lincosamide or pleuromutilin, erythromycin, spiramycin, tylosin, spiramycin, tilmicosin, lincomycin, spectinomysin, pirlimycin or tiamulin.

In a further embodiment the antimicrobial is selected from any one or more of potentiated sulphonamide mixtures, trimethoprim plus sulphadiazine, sulphadimidine, sulphadoxine, sulphadimethoxine or other sulphonamide, oxytetracycline, minocycline or doxyclycline, fluoroquinolones, enrofloxacin, ciprofloxacin, norfloxacin, danofloxacin, difloxacin or marbofloxacin.

In one embodiment the first component comprises an anti-inflammatory.

In another embodiment the anti-inflammatory is selected from any one or more of steroids such as prednisolone, betamethazone, dexamethazone, phenylbutazone, or non-steroids such as flunixin, ketoprofen, carprofen, vedaprofen, meloxicam, tepoxalin, eltenac, nimesulide or tolfenamic acid.

According to further aspect of the invention there is provided an injector device for delivery of components into the teat canal of a non-human animal comprising:
 a barrel for containing a first component,
 an outlet nozzle at one end of the barrel,
 an internal receptacle for containing a second component,
 a barrier for separating a first component and a second component, and
 a delivery means for delivery of a first component from the barrel and sequential delivery of a second component from the internal receptacle through the outlet nozzle.

In one embodiment the barrier is normally closed.

In another embodiment the barrier is releasable for delivery of the second component.

In a further embodiment the barrier is defined by at least a portion of the internal receptacle.

In one embodiment the barrier comprises one or more passageways.

In another embodiment the one or more passageways are opened when the barrier is released for delivery of the second component through said one or more passageways.

In a further embodiment the device comprises an activator for releasing the barrier.

In one embodiment the activator comprises a mechanical activator means.

In another embodiment the activator comprises at least one projecting member.

In a further embodiment the activator is located in the barrel.

In one embodiment the activator is located adjacent to the outlet nozzle.

In another embodiment the activator comprises one or more passageways.

In a further embodiment the activator is configured for engagement with the internal receptacle to provide a direct passageway for delivery of the second component from the internal receptacle into the outlet nozzle.

In one embodiment the delivery means comprises a plunger for the barrel.

In another embodiment the barrier is released by the delivery means.

In a further embodiment the internal receptacle comprises an inner barrel located within an outer barrel defined by the barrel of the injector.

In one embodiment the inner barrel is a close fit within the outer barrel.

In another embodiment the delivery means comprises the inner barrel.

In a further embodiment the inner barrel defines a plunger for the outer barrel.

In one embodiment the delivery means comprises a plunger for the inner barrel.

In another embodiment the inner barrel comprises engagement means for engagement with the outer barrel on assembly.

In a further embodiment the engagement means comprises an external seal.

In one embodiment the outer barrel comprises engagement means for engagement with the inner barrel.

In another embodiment the outer barrel comprises a locking ring for engagement with the inner barrel.

In a further embodiment the inner barrel comprises engagement means for engagement with the plunger.

In one embodiment the inner barrel comprises a locking ring for engagement with the plunger.

In another embodiment the receptacle comprises a bag.

In a further embodiment the receptacle comprises a capsule.

In one embodiment the receptacle is attached to or forms an integral part of the delivery means.

In another embodiment the activator comprises a rupturing means for at least partially releasing the barrier.

In a further embodiment the rupturing means comprises a mechanical rupture member.

In one embodiment the rupture member comprises at least one blade.

In another embodiment the rupture member comprises at least one tooth.

In a further embodiment the rupture member is located in the barrel.

In one embodiment the rupture member is located adjacent to the outlet nozzle.

In another embodiment the barrel contains a first component.

In a further embodiment the first component comprises an antimicrobial formulation.

In one embodiment the internal receptacle contains a second component.

In another embodiment the second component comprises a seal formulation.

In a further embodiment a first component is delivered from the barrel and a second component is subsequently delivered from the internal receptacle without substantial mixing of the components.

In one embodiment the seal formulation may comprise the seal formulation as described above.

In another embodiment the antimicrobial formulation may comprise the antimicrobial formulation as described above.

BRIEF DESCRIPTION OF DRAWINGS

The invention will be more clearly understood from the following description thereof given by way of example only with reference to the accompanying drawings, in which:

FIG. 5 is a cross sectional view of an external barrel of the device;

FIG. 6 is a cross sectional view of the external barrel of FIG. 5 with an antimicrobial component in place;

FIG. 7 is a cross sectional view of the assembled injector device;

FIGS. 14 (a) to 14 (c) are cross sectional views of a further injector device according to the invention in different configurations of use;

FIG. 15 is an exploded broken out view of components of the injector of FIG. 14;

FIG. 16 (a) is a detailed cross sectional view of a portion of the injector of FIG. 14, and FIGS. 16(b) and 16 (c) are detailed perspective views of a portion of the device in the configurations of FIGS. 14 (b) and (c) respectively;

FIGS. 20(a) to 20(c) are cross sectional views of the injector device of FIG. 19, in use.

DETAILED DESCRIPTION

Figure 1:
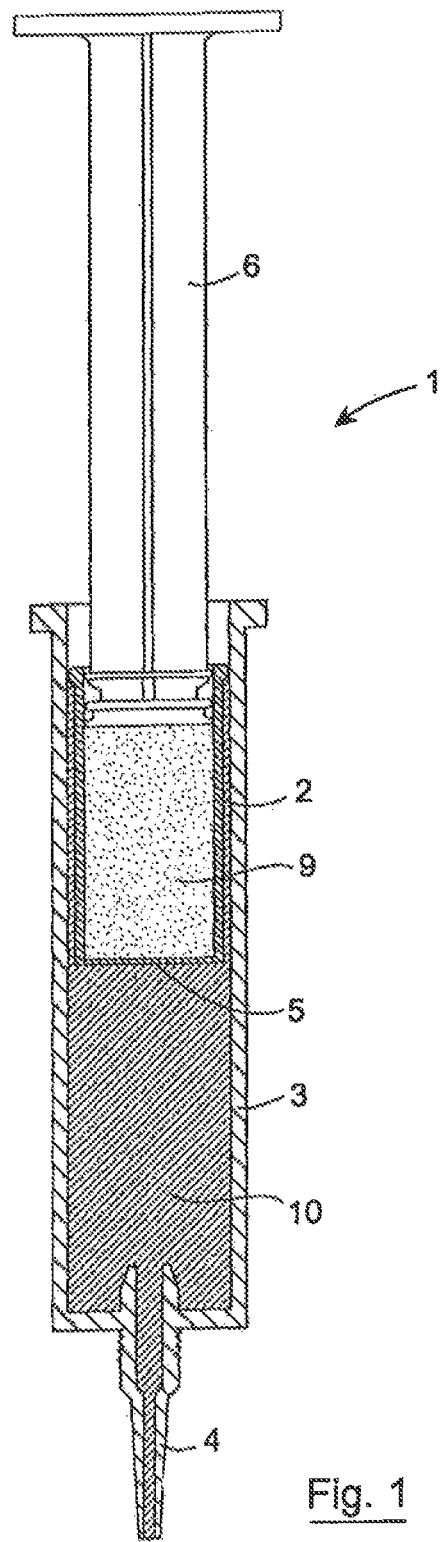
FIG. 1 is a schematic cross sectional view of an injector device according to the invention.
Figures 2, 3, 4:
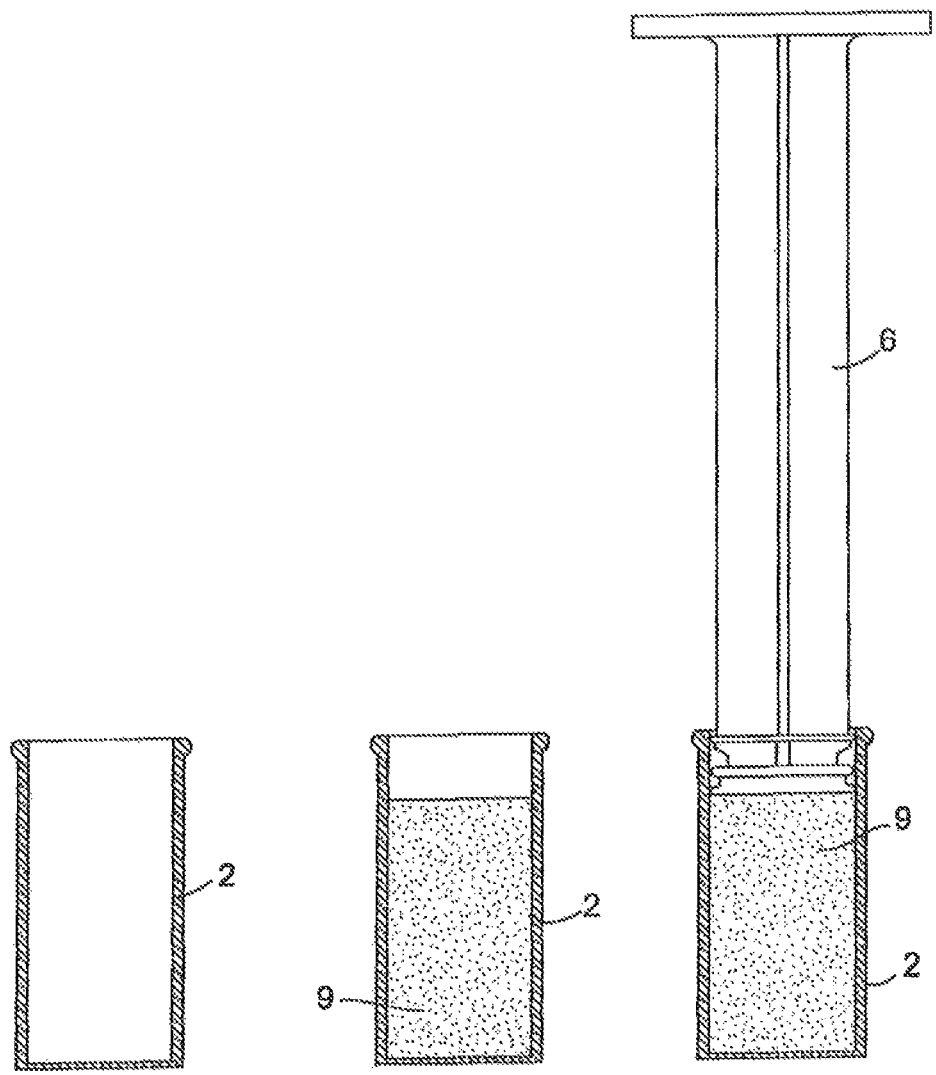
FIG. 2 is a cross sectional view of an internal barrel of the device.
FIG. 3 is a cross sectional view of the internal barrel of FIG. 2 with a seal component in place.
FIG. 4 is a cross sectional view of the internal barrel of FIG. 3 with a plunger inserted.
Figures 8A, 8B, 8C:
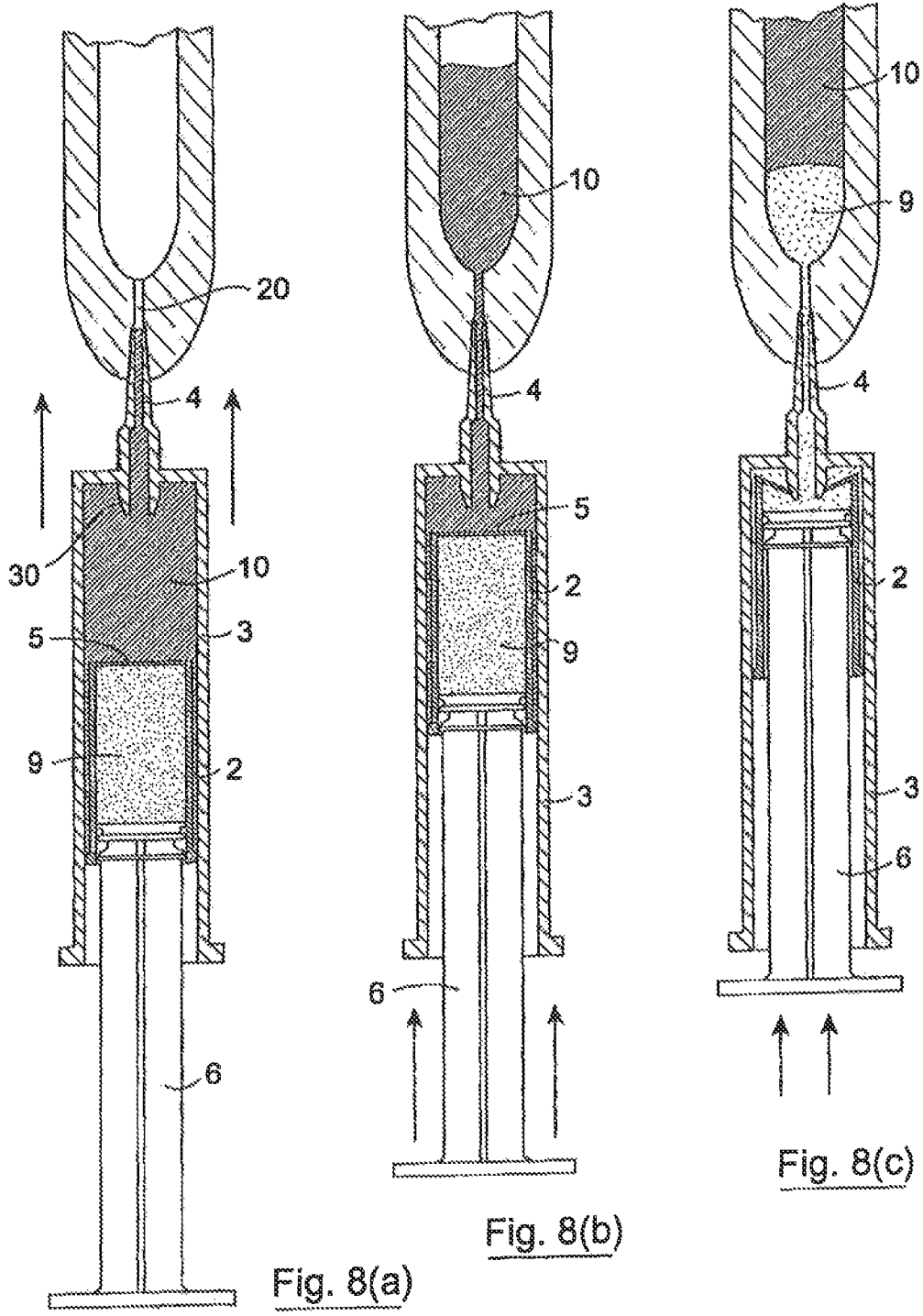
FIGS. 8(a) to 8(c) are cross sectional views of the injector device, in use.

The invention provides an injector device that allows for the sequential delivery of two incompatible components such as an antimicrobial formulation and a seal formulation into the teat canal of a nonhuman animal. The seal formulation and antimicrobial formulation are contained separately within a single injector device. This enables the product to be stored without affecting the stability of either component. The device also provides for the delivery of the antimicrobial formulation ahead of the seal formulation which effectively forms a physical barrier in the teat canal preventing any further entry into the teat canal. The seal formulation also prevents the possibility of the antimicrobial phase leaking or being expressed from the teat by gravitational or hydrostatic forces.

The seal formulation may comprise a viscous oil-based cerate containing a high proportion of a heavy metal salt, bismuth subnitrate. The product Teat Seal (trade mark of Cross Vetpharm Group) is described in detail in WO98/26759 and comprises a non-toxic heavy metal salt in a gel base. The base is a gel based on aluminium stearate. The gel preferably includes a vehicle such as liquid paraffin. The gel may also comprise a polyethylene gel. The gel may be based on low density polyethylene or on high density polyethylene. Preferably, the heavy metal salt is present in an amount of greater than 40%, preferably between 50% and 75% by weight, most preferably approximately 65% by weight.

The seal formulation prevents infection entering the udder via the teat or streak canal through a combination of its viscosity, density and adhesiveness.

The antimicrobial or anti-inflammatory formulation may be selected from any one or more of a wide variety of compounds that are known to be effective for the treatment, prevention and elimination of mastitis and mastitis-causing organisms, including inter alia gram positive and gram negative bacteria, yeasts, fungi and rickettsias. The antimicrobial or anti-inflammatory materials may include inter alia beta lactam antibiotics such as penicillins and cephalosporins, beta lactam antibiotics potentiated by beta lactamase inhibitors such as clavulanic acid, polymyxins, glycopeptides, aminoglycosides, lincosamides, macrolides, pleuromutilins, "fenicols" such as chloramphenicol and florfenicol, tetracyclines, sulphonamides and potentiated sulphonamides such as mixtures of trimethoprim and one or more sulphonamide, quinolones and fluoroquinolones, ionophores, coumarins such as novobiocin, natural or synthetic peptides, lantibiotics, and other antimicrobial products of bacteria and other microorganisms.

Other antimicrobials may be selected from any one or more of macrolide, lincosamide or pleuromutilin, erythromycin, spiramycin, tylosin, spiramycin, tilmicosin, lincomycin, spectinomysin, pirlimycin, tiamulin, potentiated sulphonamide mixtures, trimethoprim plus sulphadiazine, sulphadimidine, sulphadoxine, sulphadimethoxine or other sulphonamide, oxytetracycline, minocycline or doxyclycline, fluoroquinolones, enrofloxacin, ciprofloxacin, norfloxacin, danofloxacin, difloxacin or marbofloxacin.

The second component may be selected from any one or more of anti-inflammatory compounds, steroids such as prednisolone, betamethazone, dexamethasone, phenylbutazone, or non-steroids such as flunixin, ketoprofen, carprofen, vedaprofen, meloxicam, tepoxalin, eltenac, nimesulide or tolfenamic acid.

Other antimicrobial or anti-inflammatory compounds used in the treatment of intramammary infections in non-human animals may also be used.

These antimicrobial or anti-inflammatory materials may be formulated either singly or in combinations of two or more compounds as liquids, cerates, solutions, suspensions emulsions or flowable powders in water, oil (of animal, vegetable, mineral or other origin) or other organic vehicles. Other excipients such as solubilising, suspending or emulsifying agents, viscosity modifiers, surfactants, encapsulating agents and other means to adjust the rate at which the compound(s) is released from the formulation, buffers and such agents to maintain the pH of the formulation, anti-inflammatory agents such as various steroidal and non-steroidal compounds commonly used for this purpose, and various preservative agents commonly used in pharmaceutical preparations.

Referring to the drawings an initially to FIGS. 1 to 8 there is illustrated an injector device 1 according to the invention. The injector device 1 in this case comprises an inner barrel 2 and an outer barrel 3. The outer barrel 3 has a nozzle 4. The inner barrel 2 contains a first component comprising a seal 9. The barrel 2 has a barrier or membrane 5 at its distal end. A plunger 6 is inserted into proximal end of the inner barrel 2 above the seal component 9. An antimicrobial or anti-inflammatory component 10 is contained within the outer barrel 3 below the inner barrel 2. In use, the nozzle 4 is inserted into a teat canal 20 of a non-human animal such as a cow. The inner barrel 2 is pushed through the outer barrel 3 by the plunger 6 to expel the antimicrobial or anti-inflammatory component 10 (FIG. 8(a)). When the antimicrobial or anti-inflammatory component 10 has been expelled (FIG. 8(b)) the plunger 6 on the inner barrel 2 is further depressed to expel the seal 9 from the inner barrel 2. The pressure of the plunger 6 may be sufficient to release or rupture the barrier/membrane 5 on the inner barrel 2 allowing the seal 9 to be expelled from the injector device through the nozzle 4 and into the teat canal (FIG. 8(c)). Rupturing means such as teeth 30 situated within the outer barrel 3 adjacent to the outlet nozzle 4, may be used to release or rupture or open the barrier/membrane 5.

Figure 9:
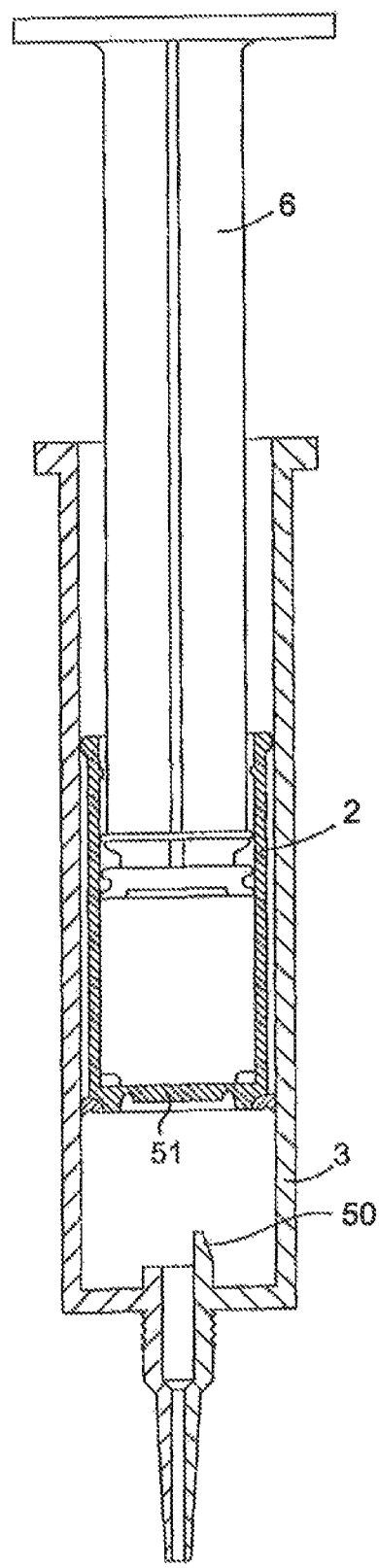
FIG. 9 is a cross sectional view of another injector of the invention.
Figure 9A:
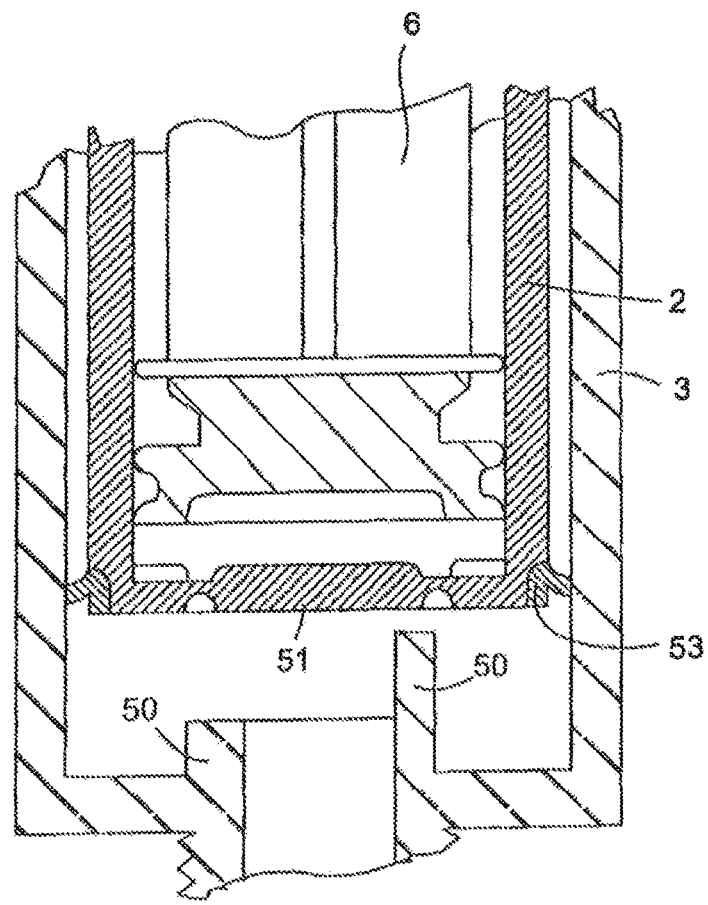
FIG. 9(a) is an enlarged view of portion of the injector in FIG. 9.
Figure 13:
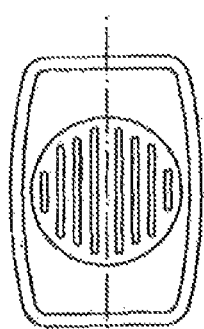
FIG. 13 is a top plan view of the device of FIG. 9.
Figure 10:
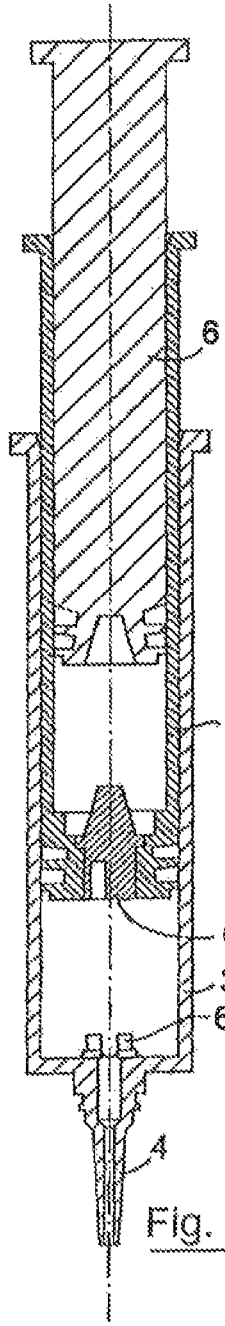
FIGS. 10 to 12 are cross sectional views of a further injector device according to the invention in different configurations of use.
Figure 11:
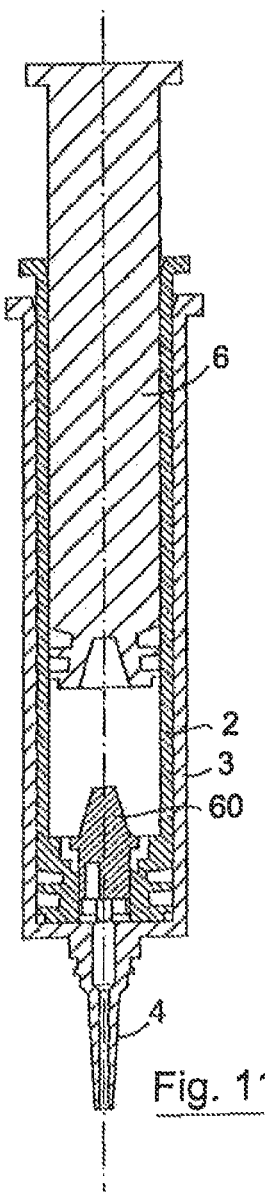
Figure 12:
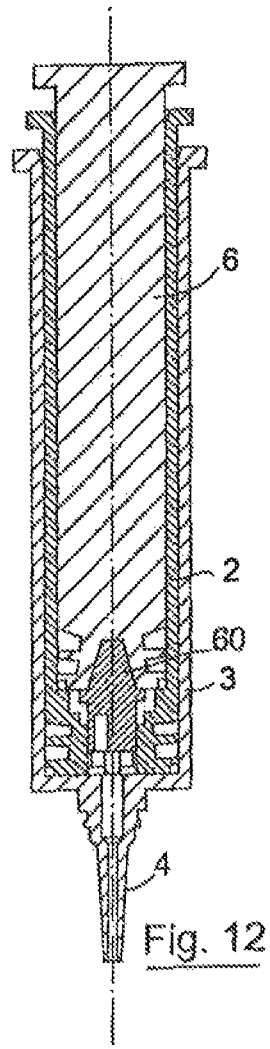

Referring to FIGS. 9 and 9 (a) there is illustrated another injector which is similar to the injector of FIGS. 1 to 8 and like parts are assigned the same reference numerals. The injector device 1 comprises an inner barrel 2 and an outer barrel 3. The outer barrel 3 has a nozzle 4. In this case the barrier is released by an activator defined by a number of spikes 50 projecting upwardly to different lengths. The membrane/barrier has a portion 51 which is knocked-out by the spikes 50 to allow ejection of the seal component. The distal end of the inner barrel 2 has a seal or frill 53 which seals with the inner wall of the outer barrel 3.

Referring to FIGS. 10 to 13 there is illustrated a further injector which is again similar to that of FIGS. 1 to 8 and like parts are assigned the same reference numerals. The injector device 1 comprises an inner barrel 2 and an outer barrel 3. The outer barrel 3 has a nozzle 4. In this case the barrier comprises a valve 60 at the distal end of the inner barrel 2. An activator 61 projects upwardly from the lower wall of the outer barrel. In use, when the inner barrel 2 is in the configuration of FIG. 11 the valve 60 is lifted by engagement with the activator 61 and allows the seal component 9 in the inner barrel 2 to pass through the injector nozzle 4.

When the plunger 6 is pushed down, the inner barrel 2 also travels down through the outer barrel 3. The outside of the inner barrel 2 is a close fit in the outer barrel 3 so that the inner barrel 2 itself acts as a delivery device or plunger for delivery of the first component from the outer barrel 3 through the nozzle 4.

Referring to FIGS. 14 to 16 there is illustrated another injector which is again similar to the injector of FIGS. 1 to 13 and like parts are assigned the same reference numerals. The injector device comprises an inner barrel 2 and an outer barrel 3. The outer barrel 3 has a nozzle 4. The inner barrel 2 contains a seal component 9. A plunger 6 is inserted into proximal end of the inner barrel 2 above the seal component 9. Antimicrobial 10 is contained within the outer barrel 3. In use, the nozzle 4 is inserted into a teat canal 20. The inner barrel 2 comprises a distal end 74 having an outlet 75 and the barrier comprises a valve 70 which is received in the outlet 75. The valve 70 is normally closed (FIGS. 14(a), (b)) during delivery of the first component from the outer barrel 3. An activator 71 projects upwardly from the lower wall of the outer barrel 3. In use, when all of the first component has been delivered and the inner barrel 2 is in the configuration of FIG. 14(c) the valve 70 is released by engagement with the activator 71 and the seal component 9 in the inner barrel 2 is allowed to pass through side passageways 76 in valve through the outlet 75 and into the injector nozzle 4.

The inner wall of the inner barrel 2 is formed for engagement with the plunger 6 and comprises a locking ring 173 between the proximal and distal ends thereof. The inner barrel 2 comprises a distal portion 178 and a proximal portion 179, the distal portion 178 having an internal diameter less than the internal diameter of the proximal portion 179. The plunger 6 comprises a seal 77 which passes over the locking ring 173 of the inner barrel on assembly and the plunger 6 is thus sealingly engaged with the inner barrel 2.

The inner barrel 2 further comprises an external seal 72 for engagement with the internal wall of outer barrel 3. The external seal 72 may for example comprise an integrally formed seal or an o-ring housed in a recess 172 in the external side wall of the inner barrel 2. The external seal 72 is located near the distal end 74 of the inner barrel.

The internal wall of the outer barrel 3 is formed for engagement with the inner barrel 2 and comprises a locking ring 73 between the proximal and distal ends thereof for engagement with the external seal 72 of the inner barrel 2. The outer barrel 3 comprises a distal portion 78 and a proximal portion 79. The distal portion 78 having an internal diameter less than the internal diameter of the proximal portion 79. The external seal 72 passes over locking ring 73 of the outer barrel 3 on assembly and sealingly engages the outer barrel. The antimicrobial or anti-inflammatory formulation 10 is thus prevented from passing between the barrels as the plunger 6 is depressed.

The valve 70 comprises a plurality of channels 76 which are exposed when the valve 70 is released to allow the seal component to pass out through the valve. Thus upon releasing of the valve the channels 76 which define a passageway for the seal component are opened.

The activator 71 defines a substantially cylindrical form defining a passageway and corresponds in form to the outlet 75 enabling it to be received in a portion of the outlet. The activator 71 is a close fit with the outlet 75.

In use the inner barrel 2 is pushed through the outer barrel 3 by the plunger 6 to expel the antimicrobial 10 (FIG. 14(a)). The outside of the inner barrel 2 has the geometry of the plunger 6 so that the inner barrel 2 itself acts as a plunger. When the antimicrobial 10 has been expelled (FIG. 14(b)) the plunger 6 on the inner barrel 2 is further depressed to expel the seal 9 from the inner barrel 2. The valve 70 is released by engagement of the inner barrel with the activator 71 and the seal component 9 in the inner barrel 2 is allowed to pass through the valve passageways into the injector nozzle 4 and is expelled into the teat canal (FIG. 14(c)).

Referring to FIGS. 14 to 16, and in particular FIGS. 16 (b) and (c) the operation of the valve is described in more details.

When closed the valve 70 which is a close fit with the outlet 75 rests in the outlet and prevents any mixing of the components in the outer and inner barrels (FIGS. 14(b) and 16(b)).

When the activator 71 is received in the outlet 75 (FIGS. 14(c) and 16(c)) the valve is released and the passageways 76 in the valve are opened to enable the seal component to pass into the valve passageways 76 through the passageway defined by the activator 71 and into the injector nozzle 4.

The engagement of the activator 71 with the outlet of the inner barrel 2 provides for alignment of the respective passageways 76 of the valve and the activator before the valve is released and the seal component is allowed to pass from the inner barrel. The respective passageways 76 of the valve and activator provide a closed and isolated pathway for the seal component to pass from the inner barrel 2 directly into the injector nozzle 4.

One advantage of a valve type barrier of this embodiment is that there is not risk of any part of the barrier becoming mobile. The barrier is retained with the injector.

Figure 17:
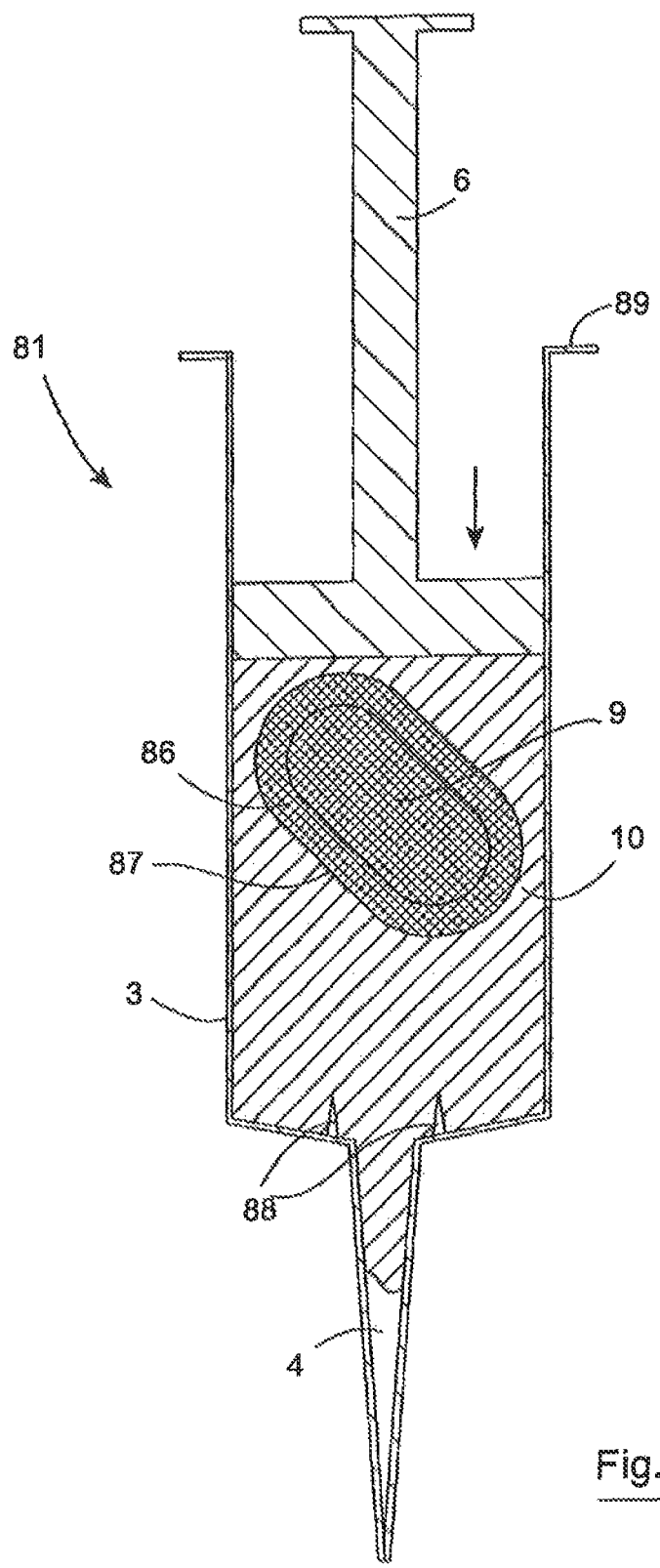
FIG. 17 is a schematic cross sectional view of an injector device according to a further embodiment of the invention.
Figure 18:
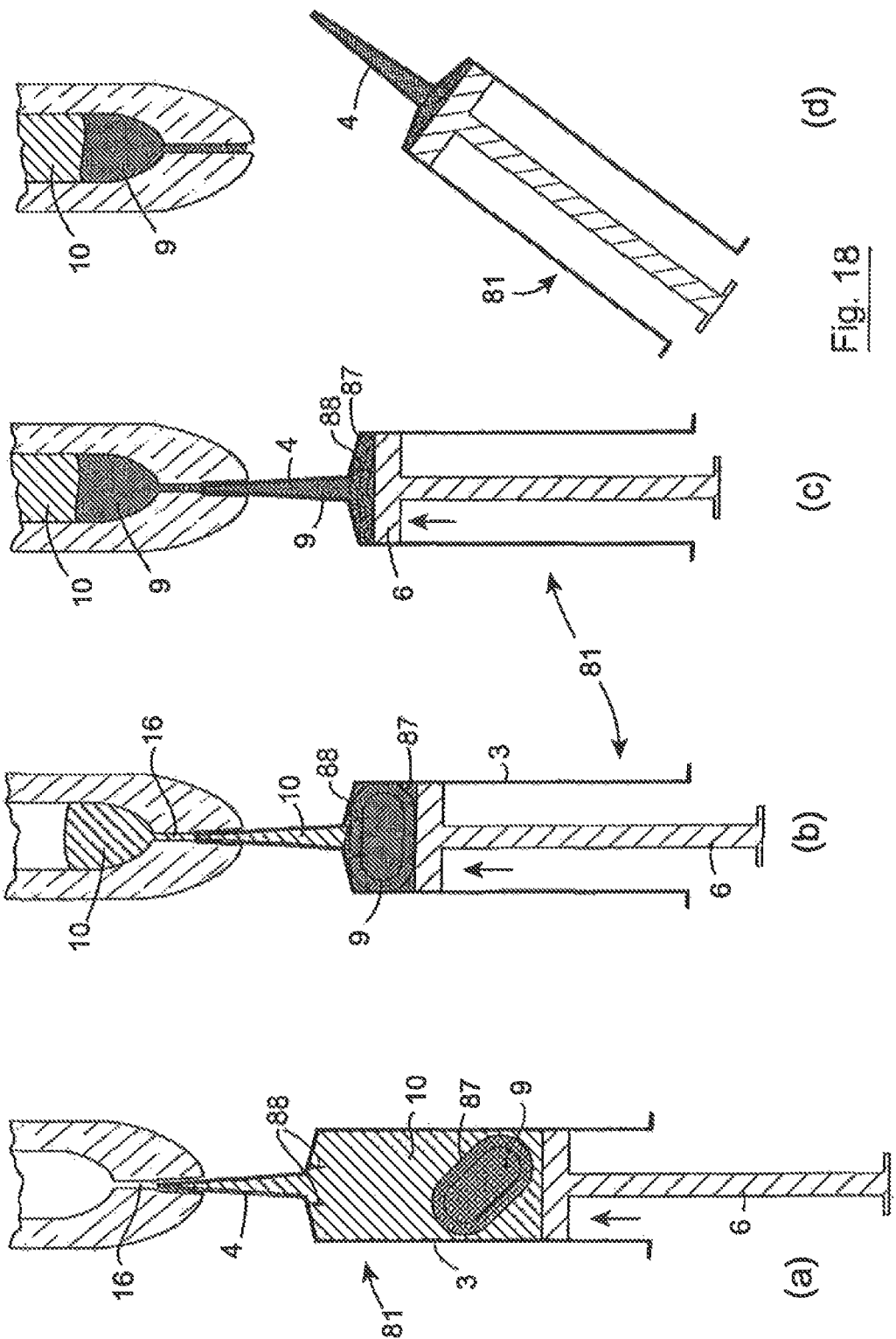
FIGS. 18(a) to 18(d) are cross sectional views of the device of FIG. 17, in use.

Referring to FIGS. 17 to 18 there is illustrated an injector device 81 of an alternative embodiment of the invention (which is similar to the injector of FIGS. 1 to 16 and like parts are assigned the same reference numerals). The injector device 81 comprises a barrel 3, an outlet nozzle 4 and a plunger 6. Two incompatible components 9 and 10 are placed within the barrel 3 of the injector device 81. The two components such as an antimicrobial 10 and a seal 9 are separated from one another by a barrier/membrane. The antimicrobial 10 is placed in the barrel 3 and a seal 9 is placed in a receptacle 86 such as a bag which is defined by an outer membrane 87 which provides the barrier.

The receptacle 86 may comprise a capsule into which the seal is filled on manufacture. The capsule may then be readily dropped into the barrel 3 of the injector before a plunger 6 is inserted.

When the nozzle 4 of the device 81 is inserted into a teat canal 16 a user depresses the plunger 6 to effect delivery of the antimicrobial 10 from the injector device into the teat canal (FIG. 17(a)). After the antimicrobial 10 is expelled from the injector device further pressure applied to the plunger results in puncturing or bursting of the receptacle 86 allowing egress of the seal 9 which is delivered into the teat canal (FIG. 17(b)). FIG. 17(d) shows the position of a seal formulation 9 and antimicrobial formulation 8 on delivery into the teat of a non-human animal.

The injector device may comprise rupturing means such as sharp teeth 88 at the distal end of the barrel 3 to assist in puncturing or bursting the receptacle 86.

It will be appreciated that for ease of manufacture and use, the receptacle 86 may be attached to the plunger 6. In this case the receptacle is unable to come into contact with the rupturing device until substantially all of the first component has been expelled from the device.

When delivering a seal 9 and antimicrobial or anti-inflammatory formulation 10 into the teat canal of a non-human animal the injector device is typically positioned vertically below the teat with the delivery nozzle uppermost. The seal formulation 9 has a much higher specific gravity than the antimicrobial or anti-inflammatory formulation 10 and therefore the receptacle containing the seal formulation remains at the lower end of the barrel 3 containing the antimicrobial or anti-inflammatory formulation during the delivery of the antimicrobial or anti-inflammatory formulation into the teat. In this case the receptacle comes into contact with the rupturing device only when substantially all of the antimicrobial or anti-inflammatory formulation has been delivered into the teat.

Figure 19:
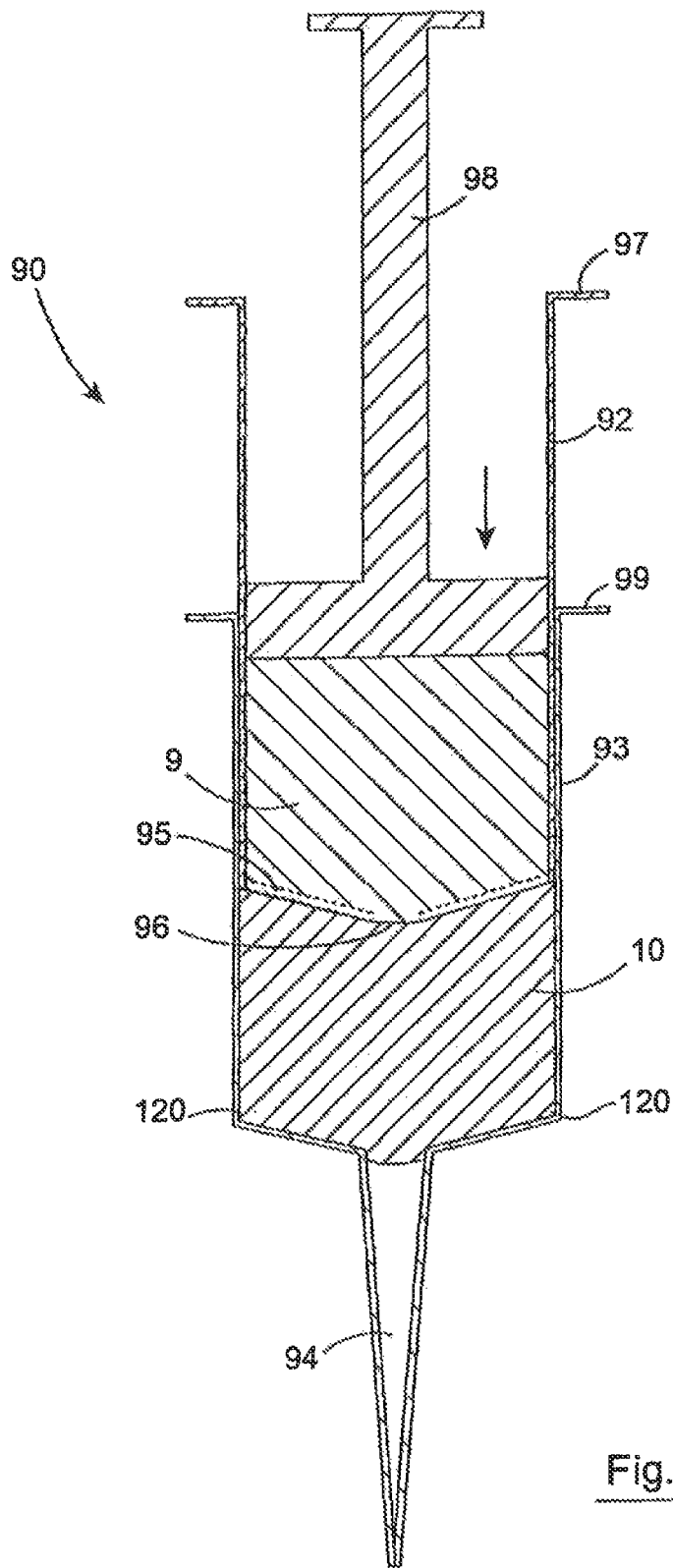
FIG. 19 is a schematic cross sectional view of another injector device according to the invention.

Referring to FIGS. 19 and 20 there is illustrated another injector device 90 of the invention. The injector device 90 comprises an inner barrel 92 and an outer barrel 93. The outer barrel 93 has a nozzle 94. The inner barrel 92 comprises a breakable/burstable barrier or membrane at its distal end and a plunger 98 at its proximal end. Antimicrobial 10 is contained within the outer barrel 93. In use, the nozzle 94 is inserted into a teat canal 16. The inner barrel 92 is pushed through the outer barrel 93 to expel the antimicrobial (FIG. 20(*b*)). This procedure may be facilitated by a flange 97 around the proximal end of the inner barrel 92 and a flange 99 around the proximal end of the outer barrel 93. When the antimicrobial 10 has been expelled (FIG. 20(*c*)) the plunger 98 on the inner barrel 92 is depressed to expel the seal 9 from the inner barrel 91. The pressure of the plunger 98 is sufficient to burst or rupture the barrier/membrane 96 on the inner barrel 92 allowing the seal 9 to be expelled from the injector device through the nozzle 94 and into the teat canal (FIG. 20(*c*)). Alternatively rupturing means such as sharp teeth situated within the outer barrel 93 at its aperture into the nozzle, ruptures the barrier/membrane 96.

A seal 96 may be provided at the front end of the inner injector barrel 92 to provide a positive seal. The inner injector may be moulded with a weak burstable barrier/membrane 95 across the outlet aperture.

It will be appreciated that the seal portion of the formulation may be manufactured in one facility and subsequently combined with the anti-bacterial portion of the formulation at a later stage, in the same or another facility.

The invention is not limited to the embodiments hereinbefore described which may be varied in detail.

The invention claimed is:

1. A method for treating, preventing, or suppressing a disease or condition in a non-human animal, the method comprising the steps of:
providing a single delivery device containing a first component and a second component for sequential delivery from the delivery device, the delivery device including an outer barrel and an inner barrel within the outer barrel, the outer barrel containing the first component, the inner barrel containing the second component, the delivery device further including a valve separating the first component and the second component;
inserting an outlet nozzle at a distal end of the outer barrel into a teat canal of the non-human animal;
pushing a plunger through the delivery device to push the inner barrel into a distal portion of the outer barrel where an inner diameter of the distal portion is smaller than an inner diameter of a proximal portion of the outer barrel, thereby delivering the first component from the delivery device through the outlet nozzle into the teat canal, the inner barrel comprising an engagement member that sealingly engages with the distal portion of the outer barrel having the inner diameter that is smaller than the inner diameter of the proximal portion of the outer barrel; and
engaging an activator with the valve to open the valve, and pushing the plunger through the inner barrel along the distal portion of the outer barrel that has the inner diameter that is smaller than the inner diameter of the proximal portion of the outer barrel, to subsequently deliver the second component from the delivery device through the outlet nozzle into the teat canal.

2. A method as claimed in claim 1 wherein the disease or condition is mastitis.

3. A method as claimed in claim 1 for treating or preventing a mastitis-causing micro-organism.

4. A method as claimed in claim 1 wherein the second component comprises a seal formulation.

5. A method as claimed in claim 4 wherein the seal formulation comprises a non-toxic heavy metal salt.

6. A method as claimed in claim 5 wherein the seal formulation comprises greater than 40% by weight of the heavy metal salt.

7. A method as claimed in claim 5 wherein the seal formulation comprises between 50% and 75% by weight of the heavy metal salt.

8. A method as claimed in claim 5 wherein the seal formulation comprises approximately 65% by weight of the heavy metal salt.

9. A method as claimed in claim 5 wherein the heavy metal salt is bismuth.

10. A method as claimed in claim 5 wherein the salt is a sub-nitrate salt.

11. A method as claimed in claim 4 wherein the seal formulation comprises a gel base.

12. A method as claimed in claim 11 wherein the gel base is a gel based on aluminium stearate.

13. A method as claimed in claim 11 wherein the gel base includes liquid paraffin as a vehicle.

14. A method as claimed in claim 1 wherein the first component comprises an antimicrobial.

15. A method as claimed in claim 14 wherein the antimicrobial includes at least one of a betalactam antibiotic, polymyxin, glycopeptide, aminoglycoside, lincosamide, macrolide, pleuromutilin, fenicol such as chloramphenicol and florfenicol, tetracycline, sulphonamide and potentiated sulphonamide such as mixtures of trimethoprim and one or more of sulphonamide, quinolone and fluoroquinolone, ionophore, courmarin such as novobiocin, natural or synthetic peptides, aminoglycoside, antimicrobial peptide or antimicrobial, lantibiotic, or other product of bacteria and other micro-organism.

16. A method as claimed in claim 15 wherein the betalactam includes at least one of penicillin, modified penicillin such as cloxacillin, amoxycillin, ampicillin, cephalosporins or beta lactam antibiotics potentiated by beta lactamase inhibitors such as clavulanic acid.

17. A method as claimed in claim 15 wherein the aminoglycoside includes at least one of streptomycin, dihydrostreptomycin, neomycin, gentamycin, framycetin, aparamycin or kanamycin.

18. A method as claimed in claim 1 wherein the first component comprises an anti-inflammatory.

19. A method as claimed in claim 18 wherein the anti-inflammatory includes at least one of a steroid such as prednisolone, betamethazone, dexamethazone, phenylbutazone, or a non-steroid such as flunixin, ketoprofen, carprofen, vedaprofen, meloxicam, tepoxalin, eltenac, nimesulide or tolfenamic acid.

20. A method as claimed in claim 1 wherein the engagement member comprises an external seal.

21. The method as claimed in claim 1 wherein the engagement member sealingly engages with a cylindrical inner surface in the distal portion of the outer barrel having the inner diameter that is smaller than the inner diameter of an inner surface formed in the proximal portion of the outer barrel.

22. A method for treating, preventing or suppressing mastitis or a mastitis causing micro-organism, the method comprising the steps of:
  providing a single delivery device containing an antimicrobial formulation and a seal formulation for sequential delivery from the delivery device, the delivery device including an outer barrel and an inner barrel within the outer barrel, the outer barrel containing the antimicrobial formulation, the inner barrel containing the seal formulation, the delivery device further including a valve separating the antimicrobial formulation and the seal formulation;
  inserting an outlet nozzle at a distal end of the outer barrel into a teat canal of a non-human animal;
  pushing a delivery member through the delivery device to deliver the antimicrobial formulation from the delivery device through the outlet nozzle into the teat canal, the delivery member comprising an engagement member at a distal end, the engagement member including an outer surface that directly contacts and sealingly engages with a cylindrical inner surface of the inner barrel at a distal portion of the inner barrel, wherein the cylindrical inner surface has an inner diameter that is smaller than an inner diameter of an inner surface formed in a proximal portion of the inner barrel; and
  engaging an activator with the valve to open the valve to sequentially deliver the seal formulation from the delivery device through the outlet nozzle into the teat canal;
  wherein the antimicrobial formulation and the seal formulation are delivered into the teat canal without substantial mixing of the formulations prior to delivery into the teat canal.

23. A method as claimed in claim 22 wherein the antimicrobial includes at least one of macrolide, lincosamide or pleuromutilin, erythromycin, spiramycin, tylosin, spiramycin, tilmicosin, lincomycin, spectinomysin, pirlimycin or tiamulin.

24. A method as claimed in claim 22 wherein the antimicrobial includes at least one of a potentiated sulphonamide mixture, trimethoprim plus sulphadiazine, sulphadimidine, sulphadoxine, sulphadimethoxine or other sulphonamide, oxytetracycline, minocycline or doxyclycline, fluoroquinolones, enrofloxacin, ciprofloxacin, norfloxacin, danofloxacin, difloxacin or marbofloxacin.

25. A method as claimed in claim 22 wherein the engagement member comprises a seal.

26. An injector device for delivery of components into the teat canal of a non-human animal, the injector device comprising:
  a barrel for containing a first component,
  an outlet nozzle configured for insertion into a teat canal at a distal end of the barrel,
  an internal receptacle within the barrel for containing a second component to be injected into the teat canal, the internal receptacle comprising an inner barrel located within an outer barrel defined by the barrel of the injector device, the inner barrel comprising a distal portion and a proximal portion, a cylindrical inner surface in the distal portion having an internal diameter that is smaller than an internal diameter of an inner surface formed in the proximal portion,
  a valve for separating the first component and the second component,
  an activator for opening the valve to allow the second component to be released from the internal receptacle, and
  a delivery member arranged to deliver the first component from the barrel of the injector device and engage the valve with the activator to open the valve for sequential delivery of the second component from the internal receptacle through the outlet nozzle, the delivery member comprising an engagement member at a distal end, the engagement member including an outer surface configured to directly contact and sealingly engage with the cylindrical inner surface in the distal portion of the inner barrel.

27. An injector device as claimed in claim 26 wherein the valve comprises one or more passageways.

28. An injector device as claimed in claim 27 wherein the one or more passageways are opened when the valve is released for delivery of the second component through said one or more passageways.

29. An injector device as claimed in claim 26 wherein the activator comprises at least one projecting member.

30. An injector device as claimed in claim 26 wherein the activator is located in the barrel of the injector device.

31. An injector device as claimed in claim 26 wherein the activator is located adjacent to the outlet nozzle.

32. An injector device as claimed in claim 26 wherein the activator comprises one or more passageways.

33. An injector device as claimed in claim 26 wherein the activator is configured for engagement with the internal receptacle to provide a direct passageway for delivery of the second component from the internal receptacle into the outlet nozzle.

34. An injector device as claimed in claim 26 wherein the delivery member comprises a plunger for the barrel of the injector device.

35. An injector device as claimed in claim 26 wherein the inner barrel is a close fit within the outer barrel.

36. An injector device as claimed in claim 26 wherein the delivery member comprises the inner barrel.

37. An injector device as claimed in claim 26 wherein the inner barrel defines a plunger for the outer barrel.

38. An injector device as claimed in claim 26 wherein the delivery member comprises a plunger for the inner barrel.

39. An injector device as claimed in claim 26 wherein:
  the engagement member comprises a seal;
  the inner barrel comprises a locking ring forming a transition between the distal portion and the proximal portion of the inner barrel; and
  the seal is configured to pass through the locking ring to sealingly engage with the distal portion of the inner barrel.

40. An injector device as claimed in claim 26 wherein the barrel of the injector device contains the first component.

41. An injector device as claimed in claim 40 wherein the first component comprises an antimicrobial formulation.

42. An injector device as claimed in claim 26 wherein the internal receptacle contains the second component.

43. An injector device as claimed in claim 42 wherein the second component comprises a seal formulation.

44. An injector device as claimed in claim 26 wherein the barrel of the injector device is configured to deliver the first component and the internal receptacle is configured to subsequently deliver the second component without substantial mixing of the components.

45. An injector device as claimed in claim 43 wherein the seal formulation comprises a non-toxic heavy metal salt.

46. An injector device as claimed in claim 45 wherein the seal formulation comprises greater than 40% by weight of the heavy metal salt.

47. An injector device as claimed in claim 45 wherein the seal formulation comprises between 50% and 75% by weight of the heavy metal salt.

48. An injector device as claimed in claim 45 wherein the seal formulation comprises approximately 65% by weight of the heavy metal salt.

49. An injector device as claimed in claim 45 wherein the heavy metal salt is bismuth.

50. An injector device as claimed in claim 45 wherein the salt is a sub-nitrate salt.

51. An injector device as claimed in claim 43 wherein the seal formulation comprises a gel base.

52. An injector device as claimed in claim 51 wherein the gel base is a gel based on aluminium stearate.

53. An injector device as claimed in claim 51 wherein the gel base includes liquid paraffin as a vehicle.

54. An injector device as claimed in claim 41 wherein the antimicrobial includes at least one of a betalactam antibiotic, polymyxin, glycopeptide, aminoglycoside, lincosamide, macrolide, pleuromutilin, fenicol such as chloramphenicol and florfenicol, tetracycline, sulphonamide and potentiated sulphonamide such as mixtures of trimethoprim and one or more of sulphonamide, quinolone and fluoroquinolone, ionophore, courmarin such as novobiocin, natural or synthetic peptides, aminoglycoside, antimicrobial peptide or antimicrobial, lantibiotic, or other product of bacteria and other micro-organism.

55. An injector device as claimed in claim 54 wherein the betalactam includes at least one of penicillin, modified penicillin such as cloxacillin, amoxycillin, ampicillin, cephalosporins or beta lactam antibiotics potentiated by beta lactamase inhibitors such as clavulanic acid.

56. An injector device as claimed in claim 54 wherein the aminoglycoside includes at least one of streptomycin, dihydrostreptomycin, neomycin, gentamycin, framycetin, aparamycin or kanamycin.

57. An injector device as claimed in claim 41 wherein the antimicrobial includes at least one of macrolide, lincosamide or pleuromutilin, erythromycin, spiramycin, tylosin, spiramycin, tilmicosin, lincomycin, spectinomysin, pirlimycin or tiamulin.

58. An injector device as claimed in claim 41 wherein the antimicrobial includes at least one of a potentiated sulphonamide mixture, trimethoprim plus sulphadiazine, sulphadimidine, sulphadoxine, sulphadimethoxine or other sulphonamide, oxytetracycline, minocycline or doxyclycline, fluoroquinolones, enrofloxacin, ciprofloxacin, norfloxacin, danofloxacin, difloxacin or marbofloxacin.

59. An injector device as claimed in claim 40 wherein the first component comprises an anti-inflammatory.

60. An injector device as claimed in claim 59 wherein the anti-inflammatory includes at least one of a steroid such as prednisolone, betamethazone, dexamethazone, phenylbutazone, or a non-steroid such as flunixin, ketoprofen, carprofen, vedaprofen, meloxicam, tepoxalin, eltenac, nimesulide or tolfenamic acid.

61. An injector device for delivery of components into the teat canal of a non-human animal, the injector device comprising:

a barrel for containing a first component,
an outlet nozzle configured for insertion into a teat canal at a distal end of the barrel,
an internal receptacle within the barrel for containing a second component to be injected into the teat canal, the internal receptacle comprising an inner barrel located within an outer barrel defined by the barrel of the injector device, the outer barrel comprising a distal portion and a proximal portion, the distal portion having an internal diameter that is smaller than an internal diameter of the proximal portion, the inner barrel comprising an engagement member arranged to engage with the distal portion of the outer barrel on assembly,
a valve for separating the first component and the second component,
an activator for opening the valve to allow the second component to be released from the internal receptacle, and
a delivery member arranged to deliver the first component from the barrel of the injector device and engage the valve with the activator to open the valve for sequential delivery of the second component from the internal receptacle through the outlet nozzle;
wherein the outer barrel comprises a locking ring forming a transition between the distal portion and the proximal portion of the outer barrel, wherein the transition is a transition between a smaller inner diameter of the distal portion and a larger inner diameter of the proximal portion; and
wherein the engagement member of the inner barrel is further configured to pass through the locking ring to sealingly engage with the distal portion of the outer barrel.

62. An injector device as claimed in claim 61 wherein the engagement member of the inner barrel comprises an external seal configured to sealingly engage with the distal portion of the outer barrel.

63. A method for providing a delivery device for delivery of components into a teat canal of a non-human animal for treating, preventing, or suppressing a disease or condition, the method comprising the steps of:

providing a first component in a barrel of a delivery device;
providing a second component in an internal receptacle within the barrel, the internal receptacle being provided with an inner barrel located within an outer barrel defined by the barrel of the delivery device, the inner barrel comprising a distal portion and a proximal portion, the distal portion having an internal diameter that is smaller than an internal diameter of the proximal portion;
separating the first component and the second component with a valve;
providing an outlet nozzle in the delivery device at one end of the barrel of the delivery device, the outlet nozzle being configured to insert into the teat canal of the non-human animal;
providing an activator in the delivery device, the activator being configured to open the valve to allow the second component to be released from the internal receptacle;
inserting a delivery member in the delivery device so that a seal on the delivery member passes through a locking ring formed in an inner surface of the inner barrel and sealingly engages with the inner barrel, the locking ring forming a transition between the distal portion and the proximal portion of the inner barrel, wherein the transition is a transition between a smaller inner diameter of the distal portion of the inner barrel and a larger inner diameter of the proximal portion of the inner barrel, the delivery member being configured to deliver the first component from the barrel of the delivery device and to engage the valve with the activator to open the valve for sequential delivery of the second component from the internal receptacle through the outlet nozzle; and inserting the inner barrel into the outer barrel so that an external seal on the inner barrel passes through a locking ring formed in an inner surface of the outer barrel and sealingly engages the outer barrel, the outer barrel comprising a distal portion and a proximal portion, the distal portion of the outer barrel having an internal diameter that is smaller than an internal diameter of the proximal portion, the locking ring formed on the outer barrel forming a transition between the distal portion of the outer barrel having the internal diameter that is smaller than the internal diameter of the proximal portion of the outer barrel and the proximal portion of the outer barrel.

64. The method as claimed in claim 63, wherein the valve is provided with one or more passageways.

65. The method as claimed in claim 63, wherein the barrel of the delivery device and the internal receptacle are configured to deliver the first component and the second component without substantial mixing of the components.

\* \* \* \* \*